US012729170B2

(12) United States Patent
Azam et al.

(10) Patent No.: US 12,729,170 B2
(45) Date of Patent: Sep. 8, 2026

(54) METHOD FOR PURIFYING 1-HEXENE

(71) Applicant: SABIC Global Technologies B.V., Bergen op Zoom (NL)

(72) Inventors: Shahid Azam, Bangalore (IN); Abdulmajeed Mohammed Al-Hamdan, Bangalore (IN); Mohammed Fahad Al-Anazi, Bangalore (IN); Bander Bawareth, Bangalore (IN); Ashim Kumar Ghosh, Bangalore (IN); Debashis Chakraborty, Bangalore (IN); Somak Paul, Bangalore (IN); Rajan V. Deshmukh, Bangalore (IN); Ahmed Hussain Eissa, Bangalore (IN); Omar A. Marghalani, Bangalore (IN); Sebastiano Licciulli, Bangalore (IN)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 224 days.

(21) Appl. No.: 18/259,962

(22) PCT Filed: Dec. 20, 2021

(86) PCT No.: PCT/EP2021/086813
§ 371 (c)(1),
(2) Date: Jun. 29, 2023

(87) PCT Pub. No.: WO2022/144208
PCT Pub. Date: Jul. 7, 2022

(65) Prior Publication Data

US 2024/0067588 A1 Feb. 29, 2024

(30) Foreign Application Priority Data

Dec. 30, 2020 (EP) .................................... 20217807

(51) Int. Cl.
*C07C 5/22* (2006.01)
*C07C 7/00* (2006.01)

(52) U.S. Cl.
CPC ............. *C07C 5/222* (2013.01); *C07C 7/005* (2013.01); *C07C 2529/40* (2013.01)

(58) Field of Classification Search
CPC ..... C07C 5/222; C07C 7/005; C07C 2529/40; C07C 2521/04; C07C 2527/054;
(Continued)

(56) References Cited

U.S. PATENT DOCUMENTS 4,104,321 A 8/1978 Ward
4,236,037 A 11/1980 Al-Chalabi
(Continued)

FOREIGN PATENT DOCUMENTS

CN 1531514 A 9/2004
CN 104549351 B 4/2015
(Continued)

OTHER PUBLICATIONS

International Search Report dated May 13, 2022 from related International Patent Application No. PCT/EP2021/086813 filed Dec. 20, 2021; 2 pages.

*Primary Examiner* — In Suk C Bullock
(74) *Attorney, Agent, or Firm* — Womble Bond Dickinson (US) LLP

(57) ABSTRACT

A method for purifying 1-hexene is disclosed. The method can include contacting a first stream containing 1-hexene and 2-ethyl-1-butene with an isomerization catalyst containing an comprising an alumina, silica-alumina, a zeolite, or an ion exchange resin, or any combinations thereof, under conditions sufficient to selectively isomerize at least a portion of 2-ethyl-1-butene into 3-methyl-2-pentene and form a second stream containing 1-hexene and 3-methyl-2-pentene,
(Continued)

and separating the second stream into a third stream containing 1-hexene and a fourth stream containing 3-methyl-2-pentene.

16 Claims, 1 Drawing Sheet

(58) Field of Classification Search
CPC ..... C07C 2529/65; C07C 5/25; C07C 5/2518; C07C 5/2568; C07C 7/04; C07C 11/107; C07C 11/113; C07C 2527/03; Y02P 20/52
See application file for complete search history.

(56) References Cited

U.S. PATENT DOCUMENTS 4,318,896 A * 3/1982 Schoonover ............ C01F 7/021 423/628
5,057,638 A 10/1991 Sweeney
5,321,193 A * 6/1994 Lin ....................... C07C 5/2512 502/355
5,863,515 A * 1/1999 Davis ........................ C01F 7/36 423/628
7,355,087 B2 4/2008 Cano et al.
8,084,659 B2 12/2011 Gartside et al.
11,377,404 B2 7/2022 Winkler et al.
2012/0310025 A1 12/2012 Wang et al.

FOREIGN PATENT DOCUMENTS

EP 0 648 721 A1 4/1995
RU 2 206 557 C1 6/2003
RU 2 254 318 C1 6/2005
WO 9510493 A1 4/1995
WO 2020 157034 A1 8/2020
WO 2020 157036 A1 8/2020

* cited by examiner

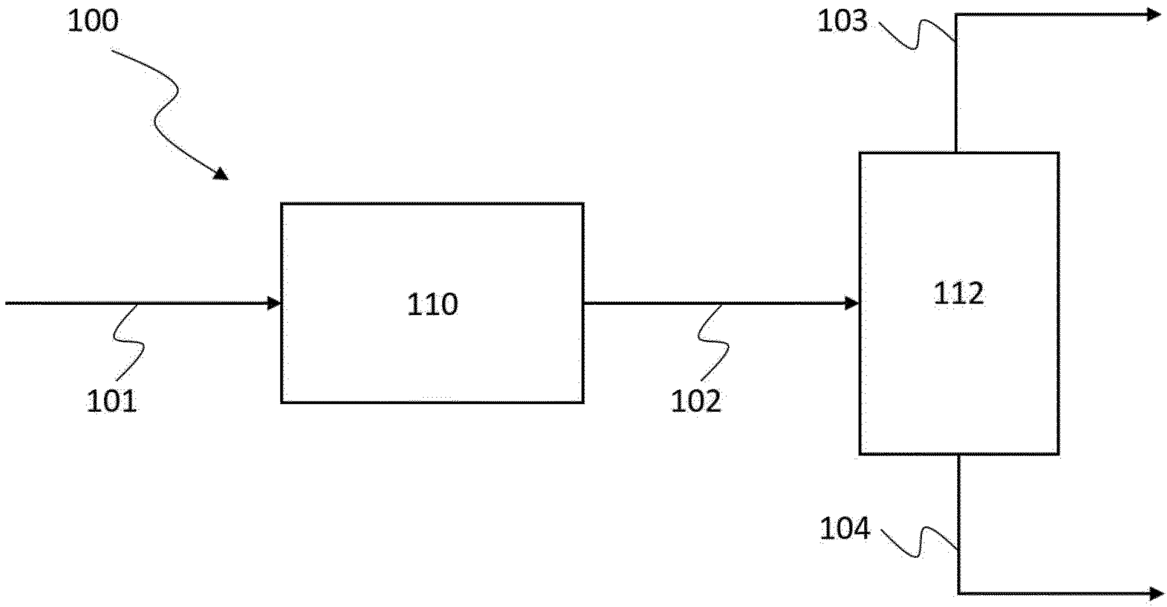
100
103
110
112
101
102
104

METHOD FOR PURIFYING 1-HEXENE

CROSS-REFERENCE TO RELATED APPLICATIONS

The present application is a 371 U.S. national stage application of International Application No. PCT/EP2021/086813, filed Dec. 20, 2021, which claims priority from European Application No. 20217807.5, filed Dec. 30, 2020, all of which are incorporated herein by reference in their entirety.

BACKGROUND OF THE INVENTION

A. Field of the Invention

The invention generally concerns systems and methods for purifying 1-hexene.

B. Description of Related Art

1-Hexene is an α-olefin compound with continuously growing demand. For example, 1-hexene can be used to prepare various high value chemicals such as high-density polyethylene (HDPE) and linear low-density polyethylene (LLDPE). HDPE and LLDPE have multiple industrial uses.

1-Hexene is typically produced by alpha olefin processes through trimerization of ethylene. However, 1-hexene only up to certain purity level, such as less than 99.5 wt. %, can be prepared by traditional alpha olefin processes. For example, US20120310025A1 discloses a method for producing 1-hexene through trimerization of ethylene. 1-hexene purity up to 97.2 wt. % is obtained by the methods disclosed.

Other attempts have been made to produce 1-hexene (see, e.g., U.S. Pat. No. 8,084,659B2, CN104549351B, U.S. Pat. No. 4,236,037A, RU2206557C1, U.S. Pat. Nos. 7,355,087B2, 4,104,321A, U.S. Pat. No. 5,057,638A). Oftentimes, these processes may suffer from increased costs and/or operating inefficiencies associated with catalyst compositions, processing conditions, and/or low purification results of 1-hexene.

SUMMARY OF THE INVENTION

A discovery has been made that provide a solution to at least one or more of the problems associated with obtaining high purity 1-hexene. Trimerization of ethylene in the alpha olefin production process can produce along with 1-hexene, 2-ethyl-1-butene as a side product. 2-ethyl-1-butene have a boiling point similar to 1-hexene, which can make it difficult to separate it from 1-hexene through traditional distillation processes. Therefore, traditional separation methods used to purify products from trimerization of ethylene can result in 1-hexene purity only up to certain percentages. In one aspect of the present invention, a catalyst containing an activated alumina, silica, silica-alumina, zeolite, and/or an ion exchange resin was discovered that can be used to selectively isomerize 2-ethyl-1-butene in presence of 1-hexene. 2-ethyl-1-butene can be isomerized into cis and trans 3-methyl-2-pentene. Cis and trans 3-methyl-2-pentene have sufficiently different boiling points than 1-hexene, which can help, in separating the isomers from 1-hexene and produce a more purified 1-hexene product stream. In some aspects, a product stream of 1-hexene can have a purity of equal to or greater than 99.5 wt. % of 1-hexene. The catalysts and processes of the present invention can be used with limited to no decrease in the overall yield of 1-hexene.

In one aspect of the present invention, a method to purify 1-hexene is described. The method can include i) contacting a first stream containing 1-hexene and 2-ethyl-1-butene with an isomerization catalyst under conditions sufficient to selectively isomerize at least a portion of 2-ethyl-1-butene into 3-methyl-2-pentene and form a second stream containing 1-hexene and 3-methyl-2-pentene, and ii) separating the second stream into a third stream containing 1-hexene and a fourth stream containing 3-methyl-2-pentene. Unless mentioned otherwise 3-methyl-2-pentene refers to cis and trans 3-methyl-2-pentene. Boiling points of 1-hexene and 2-ethyl-1-butene are 63.4° C. and 64.5° C. respectively, whereas cis and trans 3-methyl-2-pentene can have boiling points of 67.6° C. and 70.4° C., respectively. These differences in boiling points between 3-methyl-2-pentene and 1-hexene can help separate 3-methyl-2-pentene from the 1-hexene, product. In some aspects, the first stream can be contacted with the isomerization catalyst at a temperature of 40° C. to 100° C., preferably 40° C. to 60° C., a pressure of 1 bar to 10 bar, or liquid hourly space velocity (LHSV) of 0.5 $hr^{-1}$ to 10 $hr^{-1}$ or any combinations thereof. The second stream can be separated into the third stream and the fourth stream by distillation. In some aspects, the second stream can be distilled at a temperature 55° C. to 75° C. and/or pressure 0 bar to 3 bar.

In some aspects, the first stream can be obtained from a linear alpha olefin process. The linear alpha olefin process can be linear alpha olefin full range and/or on-purpose 1-hexene process. The linear alpha olefin, process can include trimerization of ethylene to produce 1-hexene. In some aspects, the reaction product from trimerization of ethylene can be purified through one or more steps to obtain the first stream. The first stream can contain 1-hexene, 2-ethyl-1-butene, optionally hexane and optionally one or more other isomers of 1-hexene. In some aspects, the first stream can contain 90 wt. % to 99.5 wt. % of 1-hexene, 0.3 wt. % to 1.5 wt. % of 2-ethyl-1-butene, optionally 0.05 wt. % to 1 wt. % of hexane, and optionally 0.1 wt. % to 1.5 wt. % of the one or more other isomers of 1-hexene. In some aspects, the second stream can contain 90 wt. % to 99.5 wt. % of 1-hexene, 0.05 wt. % to 0.5 wt. % of 2-ethyl-1-butene, 0.3 wt. % to 1.5 wt. % of 3-methyl-2-pentene, optionally 0.05 wt. % to 1 wt. % of hexane and optionally 0.1 wt. % to 1.5 wt. % of the one or more other isomers of 1-hexene. The 3-methyl-2-pentene in the second stream can be obtained by isomerization of 2-ethyl-1-butene.

The third stream can contain at least 99.5 wt. %, such as 99.5 wt. % to 99.9 wt. %, or 99.5 wt. % to 99.8 wt. %, of 1-hexene. Non-1-hexene impurities in the third stream can be less than 0.5 wt. %, such as 0 to 0.3 wt. % of 2-ethyl-1-butene, 0 to 0.3 wt. % of 3-methyl-2-pentene, 0 to 0.3 wt. % of the other isomer(s), and 0 to 0.1 wt. % of hexane. In some aspects, the optional one or more other isomers of 1-hexene can contain cis-2-hexene, trans-2-hexene, cis-3-hexene and/or trans-3-hexene.

The isomerization catalyst can contain alumina, silica, silica-alumina, a zeolite, and/or an ion exchange resin. In some aspects, the isomerization catalyst can be loaded as layered bed in the isomerization reactor, e.g. reactor in which the isomerization reaction is performed, with various combination of weight ratios of alumina, silica, silica-alumina, a zeolite, and/or an ion exchange resin. In certain aspects, the isomerization catalyst can contain alumina. The alumina used can be of various shapes, non-limiting shapes include beads, extrudates or the like. In some aspects, alumina can be shaped alumina, (e.g. beads and/or extrudate) with average particle size 1 mm to 8 mm. In some aspects, the alumina can be an activated alumina. In some aspects, the alumina, e g activated alumina can contain a modifier. In some aspects, the alumina e.g. activated alumina can have a surface area of 200 $m^2/g$ to 550 $m^2/g$. In some aspects, the alumina can contain amorphous alumina. In some aspects, the alumina can contain amorphous gamma alumina. In certain aspects, the alumina can contain a gamma alumina and/or a mixed-phase alumina containing a modifier. The alumina modifier used may alter physical and chemical properties of the alumina resulting in changing properties as adsorbent and catalyst. In some aspects, the modifier can contain materials of acidic nature such as zeolitic materials. The alumina can have at least one of, or any combination of, or all of the alumina properties described herein.

In certain aspects, the isomerization catalyst can contain a zeolite. In some aspects, the zeolite can have structure having 10 or 12 membered ring pores. In some aspects, the zeolite can be Ferrierite, ZSM-23, ZSM-11, ZSM-5, zeolite Y, zeolite Beta, or any combination thereof. In some aspects, the zeolite can have $SiO_2/Al_2O_3$ molar ratio of 2 to 1000, preferably 5 to 1000, more preferably 20 to 1000, even more preferably 150 to 1000, and also preferably 45 to 280, including all ranges therebetween and ranges between all endpoints, e.g., a range of from 2 to 5, or 5 to 20, or 45 to 1000, etc. In some aspects, the zeolite can be H form e.g. acidic form zeolite. In some aspects, the zeolite can be formed into shaped body e.g. an extrudate. In some aspects, the zeolite can contain a binder. In some particular aspects, the zeolite, such as shaped zeolite, can contain 10 wt. % to 90 wt. % of a binder. The binder can be alumina, silica-alumina, clay, or any combinations there off. In some particular aspects, the binder can be alumina. The zeolite can have at least one of, or any combination of, or all of the zeolite properties described herein. In some aspects, the isomerization catalyst can contain a zeolite catalyst and an alumina catalyst. The zeolite catalyst can contain a zeolite described herein. The alumina catalyst can contain an alumina described herein. In some particular aspects, the isomerization catalyst can contain a mixture containing the zeolite catalyst and the alumina catalyst at a wt. % ratio 10:1 to 1:10. In certain aspects, the isomerization catalyst can contain an ion exchange resin. The ion exchange resin can contain acidic sulfonic acid group. In some particular aspects, the ion exchange resin can be a polystyrene based ion exchange resin containing acidic sulfonic group. In some particular aspects, the ion exchange resin can be an acidic cationic ion exchange resins with macroporous polystyrene matrix and sulfonic acid functional groups. In some particular aspects, the ion exchange resin can be an acidic cationic ion exchange resins with macroporous styrene-divenylbenzene matrix and sulfonic acid functional groups. In some aspects, the ion exchange resin can be in hydrogen form. Certain aspects are directed to a isomerization catalyst described herein.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to other aspects of the invention. It is contemplated that any embodiment discussed herein can be implemented with respect to any method or composition of the invention, and vice versa. Furthermore, compositions and systems of the invention can be used to achieve methods of the invention.

The following includes definitions of various terms and phrases used throughout this specification.

The terms "about" or "approximately" are defined as being close to as understood by one of ordinary skill in the art. In one non-limiting embodiment, the terms are defined to be within 10%, preferably within 5%, more preferably within 1%, and most preferably within 0.5%.

The terms "wt. %," "vol. %," or "mol. %" refers to a weight percentage of a component, a volume percentage of a component, or molar percentage of a component, respectively, based on the total weight, the total volume of material, or total moles, that includes the component. In a non-limiting example, 10 grams of component in 100 grams, of the material is 10 wt. % of component.

Boiling points disclosed herein are boiling points of the respective compounds at standard atmospheric pressure (e.g., 760 mm Hg).

The term "substantially" and its variations are defined to include ranges within 10%, within 5%, within 1%, or within 0.5%.

The terms "inhibiting" or "reducing" or "preventing" or "avoiding" or any variation of these tetras, when used in the claims and/or the specification includes any measurable decrease or complete inhibition to achieve a desired result.

The term "effective," as that term is used in the specification and/or claims, means adequate to accomplish a desired, expected, or intended result.

The use of the words "a" or "an" when used in conjunction with any of the terms "comprising," "including," "containing," or "having" in the claims, or the specification, may mean "one," but it is also consistent with the meaning of "one or more," "at least one," and "one or more than one."

The phrase "and/or" means and or or. To illustrate, A, B, and/or C includes: A alone, B alone, C alone, a combination of A and B, a combination of A and C, a combination of B and C, or a combination of A, B, and C. In other words, "and/or" operates as an inclusive or.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The process and systems of the present invention can "comprise," "consist essentially of," or "consist of" particular ingredients, components, compositions, steps, etc. disclosed throughout the specification. With respect to the transitional phrase "consisting essentially of," in one non-limiting aspect, a basic and novel characteristic of the processes and the systems of the present invention are their abilities to purify 1-hexene from 2-ethyl-1-butene, having a similar boiling point as of 1-hexene.

In the context of the present invention, at least twenty embodiments are now described. Embodiment 1 is a method for purifying 1-hexene. The method includes the steps of contacting a first stream containing 1-hexene and 2-ethyl-1-butene with an isomerization catalyst comprising a modified alumina, silica-alumina, a zeolite, or an ion exchange resin, or any combinations thereof, under conditions sufficient to selectively isomerize at least a portion of 2-ethyl-1-butene into 3-methyl-2-pentene and form a second stream comprising 1-hexene and 3-methyl-2-pentene; and separating the second stream into a third stream comprising 1-hexene and a fourth stream comprising 3-methyl-2-pentene, wherein 2-ethyl-1-butene conversion for the isomerization reaction is greater than 70%, and 1-hexene conversion for isomerization reaction is less than 10%. Embodiment 2 is the embodiment of embodiment 1, wherein the isomerization condition includes a temperature of 40° C. to 60° C. Embodiment 3 is the method of any one of embodiments 1 or 2, wherein the second stream is separated by distillation at a temperature of 55° C. to 75° C. and pressure of 0 to 3 bar. Embodiment 4 is the method of any of embodiments 1 to 3, wherein the third stream contains at least 99.5 wt. % of 1-hexene, such as 99.5 wt. % to 99.8 wt. % of 1-hexene. Embodiment 5 is the method of any one of embodiments 1 to 4, wherein the first stream is obtained from a linear alpha olefin process, and/or wherein the first stream further contains hexane and one or more other isomers of 1-hexene. Embodiment 6 is the method of any one of embodiments 1 to 5, wherein the first stream comprises 90 wt. % to 99.5 wt. % of 1-hexene, 0.3 wt. % to 1.5 wt. % of 2-ethyl-1-butene, optionally 0.05 wt. % to 1 wt. % of hexane, and optionally 0.1 wt. % to 1.5 wt. % of the one or more other isomers of 1-hexene. Embodiment 7 is the method of any one of embodiments 1 to 6, wherein the second stream contains 90 wt. % to 99.5 wt. % of 1-hexene, 0.05 wt. % to 0.5 wt. % of 2-ethyl-1-butene, 0.3 wt. % to 1.5 wt. % of 3-methyl-2-pentene, optionally 0.05 wt. % to 1 wt. % of hexane, and optionally 0.1 wt. % to 1.5 wt. % of the one or more other isomers of 1-hexene. Embodiment 8 is the method of any one of embodiments 1 to 7, wherein the isomerization reaction has 2-ethyl-1-butene conversion of 80% to 99.9%, 1-hexene conversion of less than 5%, preferably less than 2%, and/or total 3-methyl-2-pentene selectivity of 50% to 100%. Embodiment 9 is the method of any one of embodiments 1 to 8, wherein the modified alumina is gamma alumina and/or a mixed-phase containing a modifier. Embodiment 10 is the method of any one of embodiments 1 to 9, wherein the zeolite is ZSM-23, ZSM-11, ZSM-5, zeolite Y, zeolite Beta, Ferrierite, or any combination thereof. Embodiment 11 is the method of any one of embodiments 1 to 10, wherein the zeolite has a $SiO_2/Al_2O_3$ molar ratio of 2 to 1000, and/or wherein the zeolite is in H-form. Embodiment 12 is the method of any one of embodiments 1 to 11, wherein the zeolite includes 10 wt. % to 90 wt. % of a binder. Embodiment 13 is the method of any one of embodiments 1 to 12, wherein the ion exchange resin contains acidic sulfonic acid group. Embodiment 14 is the method of any one of embodiments 1 to 13, wherein the ion exchange resin is a polystyrene based ion exchange resin having an acidic sulfonic group. Embodiment 15 is the method of any one of embodiments 1 to 14, wherein the isomerization catalyst includes the zeolite and the modified alumina at a weight ratio of 10:1 to 1:10. Embodiment 16 is the method of any of embodiments 1 to 15, wherein the zeolite has a $SiO_2/Al_2O_3$ molar ratio of from 5 to 1000. Embodiment 17 is the method of any of embodiments 1 to 16, wherein the zeolite has a $SiO_2/Al_2O_3$ molar ratio of from 20 to 1000. Embodiment 18 is the method of any of embodiments 1 to 17, wherein the zeolite has a $SiO_2/Al_2O_3$ molar ratio of from 45 to 280. Embodiment 19 is a method for purifying 1-hexene, the method including the steps of contacting a first stream comprising 1-hexene and 2-ethyl-1-butene with an isomerization catalyst comprising a modified alumina, silica-alumina, a zeolite, or an ion exchange resin, or any combinations thereof, under conditions sufficient to selectively isomerize at least a portion of 2-ethyl-1-butene into 3-methyl-2-pentene and form a second stream comprising 1-hexene and 3-methyl-2-pentene; and separating the second stream into a third stream comprising 1-hexene and a fourth stream comprising 3-methyl-2-pentene, wherein 2-ethyl-1-butene conversion for the isomerization reaction is greater than 70%, and 1-hexene conversion for isomerization reaction is less than 10%; wherein the isomerization conditions comprise a temperature of 40° C. to 100° C.; a pressure of 1 bar to 10 bar, or liquid hourly space velocity of 0.5 $hr^{-1}$ to 10 $hr^{-1}$, or any combinations thereof; wherein the zeolite is ZSM-23, ZSM-11, ZSM-5, zeolite Y, zeolite Beta, Ferrierite, or any combination; wherein the second stream is separated by distillation at a temperature of 55° C. to 75° C., and/or pressure of 0 to 3 bar. Embodiment 20 is the method of embodiment 19, wherein the zeolite has a $SiO_2/Al_2O_3$ molar ratio of from 2 to 1000, preferably 5 to 1000, or preferably 20 to 1000, or more preferably 2 to 5. Embodiment 21 is the method of any of embodiments 1 to 20, wherein the zeolite is ZSM-5 or zeolite Y, or any combination thereof.

Other objects, features and advantages of the present invention will become apparent from the following figures, detailed description, and examples. It should be understood, however, that the figures, detailed description, and examples, while indicating specific embodiments of the invention, are given by way of illustration only and are not meant to be limiting. Additionally, it is contemplated that changes and modifications within the spirit and scope of the invention will become apparent to those skilled in the art from this detailed description. In further embodiments, features from specific embodiments may be combined with features from other embodiments. For example, features from one embodiment may be combined with features from any of the other embodiments. In further embodiments, additional features may be added to the specific embodiments described herein.

BRIEF DESCRIPTION OF THE DRAWINGS

Advantages of the present invention may become apparent to those skilled in the art with the benefit of the following detailed description and upon reference to the accompanying drawings.

FIG. 1 is a schematic of an example of a purification process of 1-hexene in the context of the present invention.

While the invention is susceptible to various modifications and alternative forms, specific embodiments thereof are shown by way of example in the drawings. The drawings may not be to scale.

DETAILED DESCRIPTION OF THE INVENTION

A discovery has been made that provides a solution to at least one or more of the problems associated with obtaining high purity 1-hexene. In one aspect of the invention, the solution can include a method for selectively isomerizing 2-ethyl-1-butene, having boiling point(s) similar to 1-hexene, to isomers (e.g. cis and trans 3-methyl-2-pentene) of 1-hexene having boiling point(s) different compared to 1-hexene, and separating the cis and trans 3-methyl-2-pentene from 1-hexene by distillation. As shown in a non-limiting manner in the Example, methods according to one example of the present invention can produce 1-hexene with purity 99.6 wt. %.

These and other non-limiting aspects of the present invention are discussed in further detail in the following paragraphs with reference to the figures.

Referring to FIG. 1, one example of the systems and processes of the present invention for purifying 1-hexene is described. System 100 can include a reactor 110 and a separation unit 112. A first stream 101 containing 1-hexene and 2-ethyl-1-butene can be fed to the reactor 110. In the reactor 110 the first stream 101 can be contacted with an isomerization catalyst (not shown) to forma second stream 102 containing 1-hexene and 3-methyl-2-pentene. The isomerization catalyst can, include an activated alumina, a zeolite, and/or a ion exchange resin. The second stream 102 can exit the reactor 110 and can be fed to the separation unit 112. In the separation unit 112 the second stream can be separated to form a third stream containing 1-hexene and a fourth stream containing the 3-methyl-2-pentene.

The isomerization catalyst can selectively isomerize 2-ethyl-1-butene, in presence of 1-hexene (and hexane and other isomer(s) of 1-hexene, if present), to form 3-methyl-2-pentene. The reactor 110 can be a suitable reactor, including but not limited to a fixed bed reactor, moving bed, trickle-bed reactor, rotating bed reactor, slurry reactors or fluidized bed reactor. In certain aspects, the reactor 110 can be a fixed bed reactor, and can include a stationary bed containing the isomerization catalyst and the first stream 101 can be passed through and/or over the stationary bed. In the reactor 110 stream 101 can be contacted with the isomerization catalyst to selectively isomerize 2-ethyl-1-butene in the first stream into 3-methyl-2-pentene. In some aspects, catalyst containing reactor bed temperature, during the isomerization reaction (e.g. isomerization of 2-ethyl-1-butene) can be 40° C. to 60° C., or at least any one of, equal to any one of, or between any two of 40, 42, 44, 46, 48, 50, 52, 54, 56, 58, and 60° C. In some aspects, the reactor 110 inlet pressure during the isomerization reaction can be 0.5 psig to 3 psig, or at least any one of, equal to any one of, or between, any two of 0.5, 1, 1.5, 2, 2.5 and 3 psig. The first stream can be contacted with the isomerization catalyst at i) a temperature of 40° C. to 100° C., or 40° C. to 60° C., or at least any one of, equal to any one of, or between any two of 40, 42, 44, 46, 48, 50, 52, 54, 56, 58, 60, 65, 70, 75, 80, 85, 90, 95 and 100° C., ii) a pressure of 1 bar to 10 bar or at least any one of, equal to any one of, or between any two of 1, 2, 3, 4, 5, 6, 7, 8, 9 and 10 bar, and/or iii) a liquid hourly space velocity (LHSV) of 0.5 $hr^{-1}$ to 10 $hr^{-1}$, or at least any one of, equal to any one of, or between any two of 0.5, 1, 2, 3, 4, 5, 6, 7, 8, 9 and 10 $hr^{-1}$ or any combinations thereof. The 2-ethyl-1-butene conversion for the isomerization reaction can, be 50% to 100%, preferably 70% to 100%, more preferably 80% to 99.9%, or at least any one of, equal to any one of, or between any two of 50, 55, 60, 65, 70, 75, 80, 85, 90, 95, 96, 97, 97.5, 97.6, 97.8, 98, 98.5, 99, 99.5, 99.7, 99.8, 99.9 and 100%. The total selectivity 3-methyl-2-pentene for the isomerization reaction can be 50% to 100%, or at least any one of, equal to any one of, or between any two of 50, 55, 60, 65, 70, 75, 80, 85, 90, 95, 99 and 100%. 1-Hexene conversion during the isomerization reaction can be less than 10%, or less than 5%, or less than 3%, or less than 2.5%, or less than 2%, or less than 1.5%, or less than 1%, or less than 0.5%, such as 0.5% to 10%, or less than, equal to any one of, or between any two of 0.5, 1, 1.5, 2, 3, 4, 5, 6, 7, 8, 9, and 10%. In certain aspects, i) 2-ethyl-1-butene conversion for the isomerization reaction can be greater than 70%, can be greater than 80%, or greater than 90%, or greater than 95%, or greater than 97%, or greater than 97.6%, or greater than 98%, or greater than 99%, and ii) 1-hexene conversion for the isomerization reaction can be less than 10%, or less than 5%, or less than 3%, or less than 2.5%, or less than 2%, or less than 1.5%, or less than 1%, or less than 0.5%.

The isomerization catalyst can contain alumina, silica, silica-alumina, a zeolite, and/or an ion exchange resin. The isomerization catalyst can contain at least one of, any combination of, or all of alumina, silica, silica-alumina, a zeolite, and an ion exchange resin.

In some particular aspects, the isomerization catalyst can be alumina with a modifier, silica, silica-alumina, H-foam or protonic (H+) form zeolite and/or acidic sulfonic acid group containing ion exchange resin. In some aspects, the isomerization catalyst can be dried under air and/or an inert (e.g. $N_2$) atmosphere and/or flow at 120° C. to 300° C.

In certain aspects, isomerization catalyst can contain alumina. In certain aspects, the alumina can be activated alumina. In some aspects, the alumina, such as activated alumina can have i) a surface area of 200 $m^2/g$ to 550 $m^2/g$ or at least any one of, equal to any one of, or between any two of 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540 and 550 $m^2/g$, ii) average particle size, of shaped alumina, of 1 mm to 8 mm or at least any one of, equal to any one of, or between any two of 1, 2, 3, 4, 5, 6, 7 and 8 mm or iii) average crush strength of 0.5 to 40 kg, or at least any one of, equal to any one of, or between any two of 0.5, 1, 5, 10, 15, 20, 25, 30, 35 and 40 kg, or any combination thereof. In some aspects, the alumina can contain amorphous alumina. In some aspects, the alumina can contain amorphous chi and/or gamma alumina. In some aspects, the alumina can contain amorphous gamma alumina and/or mixed phase alumina, with a modifier. Non-limiting examples of commercially available activated alumina can include SELEXSORB CD available from BASF, SELEXSORB CDL available from BASF, and/or ACTISORB 100 series available from Clariant.

In certain aspects, isomerization catalyst can contain a zeolite. In some aspects, the zeolite can be ZSM-23, ZSM-11, ZSM-5, zeolite Y, zeolite Beta, Ferrierite, or any combination thereof. In some aspects, the zeolite can be in H form, e.g. acidic form. In some aspects, the zeolite can be shaped catalyst, for example bound with alumina to give cylindrical shaped extrudates. In some aspects, the zeolite can have i) structure having two or three dimensional channels with pores of 10 or 12 membered ring, ii) $SiO_2/Al_2O_3$ molar ratio of 2 to 1000, 5 to 1000, or 2 to 5, or 30 to 500, or 45 to 280, or at least any one of, equal to any one of, or between any two of 2, 5, 20, 30, 45, 50, 70, 100,_150, 200, 250, 280, 300, 400, 500, 600, 700, 800, 900 and 1000, including the endpoints, iii) medium and/or large size pores, and/or iv) a surface area of 300 $m^2/g$ to 900 $m^2/g$ or at least any one of, equal to any one of, or between any two of 300, 350, 400, 425, 450, 475, 500, 550, 600, 650, 700, 720, 740, 760, 780, 800, 850 and 900 $m^2/g$. In some aspects, the zeolite can contain 10 wt. % to 90 wt. %, or 10 wt. % to 80 wt. %, or at least any one of, equal to any one of, or between any two of 10, 15, 20, 25, 30, 35, 40, 45, 50, 55, 60, 65, 70, 75, 80, 85 and 90 wt. % of alumina as binder such as alumina, modified alumina, clay, silica-alumina, metal oxide or any combinations thereof. In some particular aspects, the zeolite can contain 10 wt. % to 90 wt. %, or 10 wt. % to 80 wt. %, of modified alumina as binder. In some particular aspects, the zeolite can be ZSM-5. In some particular aspects, the zeolite can be H-form ZSM-5 extrudate, having $SiO_2/Al_2O_3$ molar ratio of 45 to 280 and containing 15 wt. % to 25 wt. % of modified alumina as binder. Non-limiting examples of commercially available zeolite that can be used include CBV2314 from Zeolyst, CBV5524G from Zeolyst, CBV8014 from Zeolyst, CBV28014G from Zeolyst, CP914C from Zeolyst, CBV720 from Zeolyst, CBV760 from Zeolyst, or any combinations thereof.

In some aspects, the ion exchange resin can contain acidic sulfonic acid group. In some particular aspects, the ion exchange resin can be a polystyrene based ion exchange resin containing acidic sulfonic group. In some particular aspects, the ion exchange resin can be an acidic cationic ion exchange resins with macroporous polystyrene matrix and sulfonic acid functional groups. In some particular aspects, the ion exchange resin can be an acidic cationic ion exchange resins with macroporous styrene-divenylbenzene matrix and sulfonic acid functional groups. In some aspects, the ion exchange resin can in hydrogen form. In some aspects, the ion exchange resin can have i) a surface area of 10 to 100 $m^2/g$, or at least any one of, equal to any one of, or between any two of 10, 20, 30, 40, 50, 60, 70, 80, 90 and 100 $m^2/g$, ii) an average pore diameter of 200 Å to 500 Å, or at least any one of, equal to any one of, or between any two of 200, 250, 300, 350, 400, 450 and 500 Å, or iii) an average pore volume of 0.1 ml/g to 1 ml/g, or at least any one of, equal to any one of, or between any two of 0.1, 0.2, 0.3, 0.4, 0.5, 0.6, 0.7, 0.8, 0.9 and 1 ml/g, or any combinations thereof. The surface area, average pore diameter, pore volume can be measured by nitrogen BET. Non-limiting examples of commercially available ion exchange resin that can be used include DOW AMBERLYST 15 available from DowDuPont, DOW AMBERLYST 35 available from DowDuPont, DOW CSP-3 available from DowDuPont, PUROLITE CT-175 available from Purolite, PUROLITE CT-275 available from Purolite LANXESS K-2620 available from Lenntech, LANXESS K-2629 available from Lenntech or SINOCATA S-600 available from Sino Catalyst Co Limited, or any combination thereof.

In some aspects, the isomerization catalyst can contain a zeolite catalyst and an alumina catalyst. The zeolite catalyst can contain a zeolite described herein. The alumina catalyst can contain an alumina described herein. In some particular aspects, the isomerization catalyst can contain a mixture containing the zeolite catalyst and the alumina catalyst at a wt. % ratio 10:1 to 1:10, or at least any one of, equal to any one of, or between any two of 10:1, 9:2, 8:3, 7:4, 6:5, 5:5, 5:6, 4:7, 8:3, 9:2, and 10:1. In some particular aspects, the alumina catalyst can contain alumina containing a modifier. In some aspects, the isomerization catalyst can contain an ion exchange resin catalyst and an alumina catalyst. The ion exchange resin catalyst can contain an ion exchange resin described herein. In some particular aspects, the isomerization catalyst can contain a mixture containing the ion exchange resin catalyst and the alumina catalyst at a wt. % ratio 10:1 to 1:10. or at least any one of, equal to any one of, or between any two of 10:1, 9:2, 8:3, 7:4, 6:5, 5:5, 5:6, 4:7, 8:3, 9:2, and 10:1. In some particular aspects, the alumina catalyst can contain alumina containing a modifier. In some aspects, the isomerization catalyst can contain an ion exchange resin catalyst and an zeolite catalyst. In some particular aspects, the isomerization catalyst can contain a mixture containing the ion exchange resin catalyst and the zeolite catalyst at a wt. % ratio 10:1 to 1:10. or at least any one of, equal to any one of, or between any two of 10:1, 9:2, 8:3, 7:4, 6:5, 5:5, 5:6, 4:7, 8:3, 9:2, and 10:1. A non-limiting list of catalysts that can be used is provided in Table 1

TABLE 1

Non-limiting list of catalysts

| Catalyst | ZSM-5 ($SiO_2/Al_2O_3$ mole ratio 23) extrudate | ZSM-5 ($SiO_2/Al_2O_3$ mole ratio 50) extrudate | ZSM-5 ($SiO_2/Al_2O_3$ mole ratio 80) extrudate | ZSM-5 ($SiO_2/Al_2O_3$ mole ratio 280) extrudate |
|---|---|---|---|---|
| Composition | 80 wt. % of H-ZSM-5, 20 wt. % of $Al_2O_3$ | 80 wt. % of H ZSM-5, 20 wt. % of $Al_2O_3$ | 80 wt. % of H-ZSM-5, 20 wt. % of $Al_2O_3$ | 80 wt. % of H-ZSM-5, 20 wt. % of $Al_2O_3$ |
| Surface area ($m^2$/gm) | 425 | 425 | 425 | 400 |
| Commercial name and source | CBV 2314, from Zeolyst | CBV 5524G, from Zeolyst | CBV 8014, from Zeolyst | CBV 28014G, from Zeolyst |

| Catalyst | Zeolite-Y Extrudate ($SiO_2/Al_2O_3$ Mole ratio 30) | Zeolite-Y Extrudate ($SiO_2/Al_2O_3$ Mole ratio 60) | Ferrierite, Extrudate ($SiO_2/Al_2O_3$ Mole ratio 20) | Alumina |
|---|---|---|---|---|
| Composition | 80 wt. % of Zeolite-HY, 20 wt. % of $Al_2O_3$ | 80 wt. % of Zeolite-HY, 20 wt. % of $Al_2O_3$ | 80 wt. % of H-Ferrierite, 20 wt. % of $Al_2O_3$ | Alumina + modifier |
| Surface area ($m^2$/gm) | 780 | 720 | 400 | 390-410 |
| Commercial name and source | CBV 720 from Zeolyst | CBV 760 from Zeolyst | CP914C from Zeolyst | Selexsorb CD from BASF |

| Catalyst | Alumina | Alumina | Ion exchange resin |
|---|---|---|---|
| Composition | Alumina + modifier | | Styrene--divinylbenzene with Sulfonic acid functional group |
| Surface area ($m^2$/gm) | 450-460 | | 53 |
| Commercial name and source | SELEXSORB CDL from BASF | ACTISORB 100-1 from Clariant | AMBERLYST-15 from Dupont |

In some aspects, catalyst active site can be inaccessible to reactant molecule due to deposition of C-species or pore blockage resulting in activity decline with time-on-stream; and the catalyst in the reactor is known as spent or deactivated catalyst. In some aspect, the spent isomerization catalyst can be regenerated from the spent catalyst by contacting with nitrogen ($N_2$) or diluted oxygen ($O_2$) at 150° C. to 500° C. to regenerate the catalyst. In certain aspects, the spent catalyst can be contacted with nitrogen ($N_2$) flow at 150° C. to 350° C. preferably at 270-290° C. for 15 hrs to 30 hrs. Regeneration conditions may depend on the catalyst type (e.g. composition).

The separation unit 112 can include a distillation column. The second stream 102 can be separated by distillation in the distillation column to form the third stream 103 containing 1-hexene and the fourth stream 104 containing 3-methyl-2-pentene. The distillation column operation conditions for separation of the second stream 102 can include i) a temperature of 50° C. to 100° C., or 55° C. to 75° C., or at least any one of, equal to any one of, or between any two of 50, 55, 60, 65, 70, 75, 80, 85, 90, 95 and 100° C., ii) a pressure of 0 bar to 3 bar, or at least any one of, equal to any one of, or between any two of 0, 0.01, 0.1, 0.5, 1, 1.5, 2, 2.5 and 3 bar. The boiling points of cis and trans 3-methyl-2-pentene, are different enough from 1-hexene, such that through distillation of the second stream, 3-methyl-2-pentene can be separated from 1-hexane. In some aspects, the third stream 103 can be formed as the top distillate of the distillation column and the fourth stream 104 can be formed as the bottom distillate of the distillation column.

The first stream 101 can be obtained from an alpha olefin process. The alpha olefin process linear alpha olefin full range and/or on-purpose 1-hexene process. The alpha olefin process can include trimerization of ethylene to form 1-hexene. The ethylene can be trimerized using a suitable process and catalyst known in the art. In some aspects, the 1-hexene obtained by trimerization of ethylene can be purified by one or more steps to obtain the first stream. The first stream can contain i) 90 wt. % to 99.5 wt. %, or 95 wt. % to 99.5 wt. %, or at least any one of, equal to any one of, or between any two of 90, 90.5, 91, 91.5, 92, 92.5, 93, 93.5, 94, 94.5, 95, 95.5, 96, 96.5, 97, 97.5, 98, 98.5, 99, and 99.5 wt. % of 1-hexene, and 0.3 wt. % to 1.5 wt. % or at least any one of, equal to any one of, or between any two of 0.3, 0.5, 0.6, 0.7, 0.8, 0.9, 1, 1.1, 1.2, 1.3, 1.4 and 1.5 wt. % of 2-ethyl-1-butene. The first stream 101 can optionally contain 0.05 wt. % to 1 wt. % of hexane and 0.1 wt. % to 1.5 wt. % of one or more other isomers of 1-hexene. In some aspects, one or more other isomers of 1-hexene can contain cis-2-hexene, trans-2-hexene, cis-3-hexene and/or trans-3-hexene. 2-ethyl-1-butene, hexane and the other isomers) in the first stream 101 can be formed as side products in the alpha olefin process.

The second stream 102 can contain i) 90 wt. % to 99.5 wt. %, or 95 wt. % to 99.5 wt. %, or at least any one of, equal to any one of, or between any two of 90, 90.5, 91, 91.5, 92, 92.5, 93, 93.5, 94, 94.5, 95, 95.5, 96, 96.5, 97, 97.5, 98, 98.5, 99, and 99.5 wt. % of 1-hexene, ii) 0.05 wt. % to 0.5 wt. % or at least any one of, equal to any one of, or between any two of 0.05, 0.1, 0.15, 0.2, 0.25, 0.3, 0.35, 0.4, 0.45, and 0.5 wt. % of 2-ethyl-1-butene, and iii) 0.3 wt. % to 1.5 wt. %, or at least any one of, equal to any one of, or between any two of 0.3, 0.5, 0.6, 0.7, 0.8, 0.9, 1, 1.1, 1.2, 1.3, 1.4 and 1.5 wt. % of 3-methyl-2-pentene. At least a portion of the 2-ethyl-1-butene from the first stream can isomerize in the reactor 110 to form at least a portion of 3-methyl-2-pentene in the second stream 102. The second stream 102 can optionally contain 0.05 wt. % to 1 wt. % of hexane and 0.1 wt. % to 1.5 wt. % of one or more other isomers of 1-hexene.

The third stream 103 can contain at least 99.5 wt. %, or 99.5 wt. % to 99.9 wt. %, or 99.5 wt. % to 99.8 wt. %, or at least any one of, equal to any one of, or between any two of 99.5, 99.6, 99.7, 99.8, and 99.9 wt. % of 1-hexene. Impurities in the third stream 103 can be less than 0.5 wt. %, or less than 0.4 wt. %, or less than 0.3 wt. %, or less than 0.2 wt. %, or less than 0.1 wt. %, or 0 to 0.5 wt. %, or 0.1 wt. % to 0.5 wt. %. The impurities in the third stream 103 can include 2-ethyl-1-butene, hexane, 3-methyl-2-pentene and the one or more other isomer(s). In some aspects, the third stream can further contain 0 to 0.3 wt. % of 2-ethyl-1-butene, 0 to 0.3 wt. % of 3-methyl-2-pentene, 0 to 0.3 wt. % of the other isomer(s), and 0 to 0.1 wt. % of hexane. In certain aspects, the 1-hexene from the third stream 103 can be used to produce HDPE and LLDPE.

The fourth stream 104 can contain at least a portion of the other isomer(s), and hexane, if present, from the second stream 102. In some aspects, the fourth stream 104 can also contain a portion 1-hexene from the second stream.

In FIG. 1 the reactors, units and/or zones can include one or more heating and/or cooling devices (e.g., insulation, electrical heaters, jacketed heat exchangers in the wall) and/or controllers (e.g., computers, flow valves, automated values, etc.) that can be used to control the reaction temperature and pressure of the reaction mixture. While only one unit or zone is shown, it should be understood that multiple reactors or zones can be housed in one unit or a plurality of reactors housed in one heat transfer unit.

EXAMPLES

The present invention will be described in greater detail by way of specific examples. The following examples are offered for illustrative purposes only, and are not intended to limit the invention in any manner Those of skill in the art will readily recognize a variety of noncritical parameters which can be changed or modified to yield essentially the same results.

Example 1

Method for Purifying 1-Hexene

1-Hexene obtained from an alpha olefin process (e.g., ethylene trimerization process) was purified according to one example of the present invention. A stream, stream 1, from the ethylene trimerization process, containing 1-hexene, and 2-ethyl-1-butene was fed to a reactor. The reactor contained a isomerization catalyst containing SELEXSORB CD, H-form ZSM-5 ($SiO_2/Al_2O_3$ ratio 50), and AMBERLYST 15. The stream 1 was contacted with the isomerization catalyst in the reactor at 60° C. to selectively isomerize 2-ethyl-1-butene and form cis and trans 3-methyl-2-pentene. A stream, stream 2, containing the 1-hexene and cis and trans 3-methyl-2-pentene formed from the reactor was fed to a distillation, column. Stream 2 was distilled in the distillation column. A stream, stream 3, containing highly pure 1-hexene, 99.6 wt. %, was obtained as a top distillate from the distillation column. A stream, stream 4, containing the cis and trans 3-methyl-2-pentene, was obtained as a bottom distillate from the distillation column. The compositions of streams 1, 2, 3 and 4 are provided in table 2.

TABLE 2

| | Unit | Stream 1 | Stream 2 | Stream 3 | Stream 4 |
|---|---|---|---|---|---|
| 2-Ethyl-1-Butene | wt. % | 0.94 | 0.16 | 0.15 | 0.3 |
| Cis-3-Methyl-2-Pentene | wt. % | 0.00 | 0.45 | 0.15 | 6.07 |
| Trans-3-Methyl-2-Pentene | wt. % | 0.00 | 0.30 | 0.01 | 5.72 |
| Cis-2-Hexene | wt. % | 0.36 | 0.36 | 0.04 | 6.38 |
| Cis-3-Hexene | wt. % | 0.02 | 0.02 | 0.01 | 0.18 |
| Trans-2-Hexene | wt. % | 0.30 | 0.30 | 0.07 | 4.58 |
| Trans-3-Hexene | wt. % | 0.04 | 0.04 | 0.02 | 0.53 |
| Hexane | wt. % | 0.13 | 0.13 | 0.01 | 2.3 |
| 1-Hexene | wt. % | 98.21 | 98.21 | 99.6 | 73.94 |

Example 2

Isomerization of 2-ethyl-1-butene

Catalysts used in Example 2 were tested using 1-hexene feed containing 2-ethyl-1-butene (see feed composition in Table 3) using stainless steel tubular flow reactor. For each test 7.00 ml catalyst (sized to 20-40 mesh) was loaded in reactor and was dried at 150 deg C. overnight under $N_2$ flow. The 1-hexene feed was introduced at 1.0 ml/min and the reactor effluent was analyzed to determine the conversions of 2-ethyl-1-butene and 1-hexene. The test data obtained after about 3 hours time-on-stream are shown in Table 3. 2-ethyl-1-butene from feed streams containing 1-hexene and 2-ethyl-1-butene were isomerized to form cis and trans 3-methyl-2-pentene, using catalysts as described in Table 3. Reaction conditions and results for the experiments are described in Table 3. As can be seen from Table 3, 2-ethyl-1-butene conversion above 97% can be obtained using zeolite and ion-exchange resin catalysts. Further, alumina catalysts (experiment 8) can result in 2-ethyl-1-butene conversion of 94.55%.

TABLE 3

| | Experiment 1 | Experiment 2 | Experiment 3 | Experiment 4 | Experiment 5 |
|---|---|---|---|---|---|
| Catalyst type | Zeolite | Zeolite | Zeolite | Zeolite | Zeolite |
| Commercial Source | Zeolyst | Zeolyst | Zeolyst | Zeolyst | Zeolyst |
| Commercial Product Name | CBV2314, extrudate | CBV5524G, extrudate | CBV8014, extrudate | CBV28014G, extrudate | CP914C, extrudate |
| Catalyst Description | 80 wt % HZSM-5, 20 wt % $Al_2O_3$ | 80 wt % HZSM-5, 20 wt % $Al_2O_3$ | 80 wt % HZSM-5, 20 wt % $Al_2O_3$ | 80 wt % HZSM-5, 20 wt % $Al_2O_3$ | 80 wt % H-Ferrierite, 20 wt % $Al_2O_3$ |
| Catalyst Volume, ml | 7.00 | 7.00 | 7.00 | 7.00 | 7.00 |
| Catalyst Weight, g | 4.60 | 4.45 | 4.80 | 4.79 | 5.20 |
| Feed (1-hexene, 2E1B) Rate, ml/min | 1.00 | 1.00 | 1.00 | 0.60 | 1.00 |
| Space Velocity, LHSV (hr − 1) | 8.57 | 8.57 | 8.57 | 5.14 | 8.57 |
| Catalyst Bed Temperature, deg C. | 45.00 | 45.00 | 45.00 | 50.00 | 45.00 |
| Reactor Inlet Pressure, psig | 1.50 | 1.50 | 1.50 | 1.50 | 1.50 |
| Time-on-stream, hr | 2.97 | 3.03 | 3.06 | 2.92 | 3.09 |
| Reactor Feed Composition, wt % | | | | | |
| 1-Hexene | 98.15 | 98.20 | 98.36 | 98.19 | 98.15 |
| 2-ethyl-1-butene | 1.18 | 1.14 | 1.24 | 1.16 | 1.18 |
| Hexane | 0.02 | 0.02 | 0.00 | 0.02 | 0.02 |
| Trans-3-hexene | 0.03 | 0.03 | 0.03 | 0.03 | 0.03 |
| Cis-3-hexene | 0.01 | 0.01 | 0.01 | 0.01 | 0.01 |
| Trans-2-hexene | 0.10 | 0.09 | 0.17 | 0.09 | 0.10 |
| Cis-3-methyl-2-pentene | 0.24 | 0.23 | 0.06 | 0.23 | 0.24 |
| Cis2-hexene | 0.03 | 0.03 | 0.03 | 0.03 | 0.03 |
| Trans-3-methyl-2-pentene | 0.22 | 0.21 | 0.01 | 0.21 | 0.22 |
| Total wt % | 99.97 | 99.96 | 99.90 | 99.96 | 99.97 |
| Reactor Effluent Composition, wt. % | | | | | |
| 1-Hexene | 77.44 | 95.65 | 88.11 | 97.86 | 88.70 |
| 2-ethyl-1-butene | 0.01 | 0.01 | 0.03 | 0.10 | 0.01 |
| Hexane | 0.18 | 0.19 | 0.03 | 0.16 | 0.18 |
| Trans-3-hexene | 1.66 | 0.19 | 0.65 | 0.05 | 0.81 |
| Cis-3-hexene | 0.17 | 0.04 | 0.07 | 0.01 | 0.09 |
| Trans-2-hexene | 12.13 | 1.42 | 5.72 | 0.25 | 6.41 |
| 2-methyl-2-pentene | 0.00 | 0.00 | 0.00 | 0.00 | 0.00 |
| Cis-3-methyl-2-pentene | 0.45 | 0.49 | 0.40 | 0.49 | 0.46 |

TABLE 3-continued

| | | | | | |
|---|---|---|---|---|---|
| Cis2-hexene | 6.95 | 0.98 | 4.06 | 0.19 | 2.34 |
| Trans-3-methyl-2-pentene | 0.92 | 1.01 | 0.81 | 0.87 | 0.94 |
| Total, wt % | 99.89 | 99.98 | 99.87 | 99.97 | 99.94 |
| Conversions | | | | | |
| 1-Hexene Conversion, wt % | 21.10 | 2.59 | 8.53 | 1.19 | 9.63 |
| 2-Ethyl-1-Butene, wt. % | 99.05 | 99.44 | 97.78 | 97.67 | 99.46 |

| | Expt. 6 | Expt. 7 | Expt. 8 | Expt. 10 | Expt. 11 |
|---|---|---|---|---|---|
| Catalyst type | Zeolite | Zeolite | Alumina | Alumina | Ion exchange resin |
| Commercial Source | Zeolyst | Zeolyst | BASF | Criterion | |
| Commercial Product Name | CBV720, extrudate | CBV760, extrudate | Selexsorb CD | Actisorb 100-1 | Amberlyst-15 |
| Catalyst Description | 80 wt % Zeolite HY, 20 wt % $Al_2O_3$ | 80 wt % Zeolite HY, 20 wt % $Al_2O_3$ | Alumina + modifier | | Styrene-DVB with Sulfonic acid functional group |
| Catalyst Volume, ml | 7.00 | 7.00 | 7.00 | 7.00 | 7.00 |
| Catalyst Weight, g | 4.51 | 5.20 | 4.60 | 3.66 | 4.13 |
| Feed (1-hexene, 2E1B) Rate, ml/min | 1.00 | 1.00 | 1.00 | 1.00 | 1.00 |
| Space Velocity, LHSV (hr − 1) | 8.57 | 8.57 | 8.57 | 8.57 | 8.57 |
| Catalyst Bed Temperature, deg C. | 45.00 | 45.00 | 45.00 | 45.00 | 45.00 |
| Reactor Inlet Pressure, psig | 1.50 | 1.50 | 1.50 | 1.50 | 1.50 |
| Time-on-stream, hr | 3.15 | 2.91 | 2.99 | 2.94 | 2.89 |
| Reactor Feed Composition, wt % | | | | | |
| 1-Hexene | 98.15 | 98.36 | 98.19 | 98.36 | 98.36 |
| 2-ethyl-1-butene | 1.18 | 1.24 | 1.16 | 1.24 | 1.24 |
| Hexane | 0.02 | 0.00 | 0.02 | 0.00 | 0.00 |
| Trans-3-hexene | 0.03 | 0.03 | 0.03 | 0.03 | 0.03 |
| Cis-3-hexene | 0.01 | 0.01 | 0.01 | 0.01 | 0.01 |
| Trans-2-hexene | 0.10 | 0.17 | 0.09 | 0.17 | 0.17 |
| Cis-3-methyl-2-pentene | 0.24 | 0.06 | 0.23 | 0.06 | 0.06 |
| Cis2-hexene | 0.03 | 0.03 | 0.03 | 0.03 | 0.03 |
| Trans-3-methyl-2-pentene | 0.22 | 0.01 | 0.21 | 0.01 | 0.01 |
| Total wt % | 99.97 | 99.90 | 99.96 | 99.90 | 99.90 |
| Reactor Effluent Composition, wt. % | | | | | |
| 1-Hexene | 87.26 | 79.23 | 98.21 | 98.38 | 96.50 |
| 2-ethyl-1-butene | 0.00 | 0.02 | 0.06 | 1.22 | 0.03 |
| Hexane | 0.19 | 0.04 | 0.16 | 0.00 | 0.03 |
| Trans-3-hexene | 0.43 | 1.12 | 0.03 | 0.03 | 0.18 |
| Cis-3-hexene | 0.05 | 0.11 | 0.01 | 0.01 | 0.02 |
| Trans-2-hexene | 5.29 | 9.69 | 0.09 | 0.16 | 1.15 |
| 2-methyl-2-pentene | 0.00 | 0.00 | 0.00 | 0.00 | 0.00 |
| Cis-3-methyl-2-pentene | 0.36 | 0.34 | 0.52 | 0.06 | 0.39 |
| Cis2-hexene | 5.63 | 8.62 | 0.03 | 0.03 | 0.79 |
| Trans-3-methyl-2-pentene | 0.73 | 0.68 | 0.83 | 0.01 | 0.79 |
| Total, wt % | 99.93 | 99.84 | 99.94 | 99.89 | 99.89 |
| Conversions | | | | | |
| 1-Hexene Conversion, wt % | 11.10 | 19.45 | 0.00 | 0.00 | 1.89 |
| 2-Ethyl-1-Butene, wt. % | 99.65 | 98.16 | 94.55 | 1.46 | 97.58 |

Although embodiments of the present application and their advantages have been described in detail, it should be understood that various changes, substitutions and alterations can be made herein without departing from the spirit and scope of the embodiments as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the above disclosure, processes, machines, manufacture, compositions of matter, means, methods, or steps, presently existing or later to be developed that perform substantially the same function or achieve substantially the same result as the corresponding embodiments described herein can be utilized. Accordingly, the appended claims are intended to include within their scope such processes, machines, manufacture, compositions of matter, means, methods, or steps.

The invention claimed is:

1. A method for purifying 1-hexene, the method comprising:

contacting a first stream comprising 1-hexene and 2-ethyl-1-butene with an isomerization catalyst comprising activated alumina having a surface area of 200 $m^2/g$ to 550 $m^2/g$ under conditions sufficient to selectively isomerize at least a portion of 2-ethyl-1-butene into 3-methyl-2-pentene and form a second stream comprising 1-hexene and 3-methyl-2-pentene; and separating the second stream into a third stream comprising 1-hexene and a fourth stream comprising 3-methyl-2-pentene, wherein 2-ethyl-1-butene conversion for the isomerization reaction is greater than 70%, and 1-hexene conversion for isomerization reaction is less than 10% wherein the isomerization conditions comprise a temperature of 40° C. to 100° C.; a pressure of 1 bar to 10 bar, or liquid hourly space velocity of 0.5 $hr^{-1}$ to 10 $hr^{-1}$, or any combinations thereof; and wherein the second stream is separated by distillation at a temperature of 55° C. to 75° C., and/or pressure of 0 to 3 bar.

2. The method of claim 1, wherein the isomerization condition comprises a temperature of 40° C. to 60° C.

3. The method of claim 1, wherein the third stream comprises at least 99.5 wt. % of 1-hexene.

4. The method of claim 1, wherein the first stream is obtained from a linear alpha olefin process, and/or wherein the first stream further comprises hexane and one or more other isomers of 1-hexene.

5. The method of claim 1, wherein the first stream comprises 90 wt. % to 99.5 wt. % of 1-hexene, 0.3 wt. % to 1.5 wt. % of 2-ethyl-1-butene, optionally 0.05 wt. % to 1 wt. % of hexane, and optionally 0.1 wt. % to 1.5 wt. % of the one or more other isomers of 1-hexene.

6. The method of claim 1, wherein the second stream comprises 90 wt. % to 99.5 wt. % of 1-hexene, 0.05 wt. % to 0.5 wt. % of 2-ethyl-1-butene, 0.3 wt. % to 1.5 wt. % of 3-methyl-2-pentene, optionally 0.05 wt. % to 1 wt. % of hexane, and optionally 0.1 wt. % to 1.5 wt. % of the one or more other isomers of 1-hexene.

7. The method of claim 1, wherein the isomerization reaction has 2-ethyl-1-butene conversion of 80% to 99.9%, 1-hexene conversion of less than 5%, and/or total 3-methyl-2-pentene selectivity of 50% to 100%.

8. The method of claim 1, wherein the isomerization catalyst further comprises a zeolite, and the zeolite is ZSM-5 or zeolite Y, or any combination thereof.

9. The method of claim 8, wherein the zeolite has a $SiO_2/Al_2O_3$ molar ratio of 2 to 1000, and/or wherein the zeolite is in H-form.

10. The method of claim 8, wherein the zeolite comprises 10 wt. % to 90 wt. % of a binder.

11. The method of claim 8, wherein the isomerization catalyst comprises the zeolite and the alumina at a weight ratio of 10:1 to 1:10.

12. The method of claim 8, wherein the zeolite has a $SiO_2/Al_2O_3$ molar ratio of from 5 to 1000.

13. The method of claim 8, wherein the zeolite has a $SiO_2/Al_2O_3$ molar ratio of from 20 to 1000.

14. The method of claim 1, wherein the alumina has an average particle size of 1 mm to 8 mm.

15. The method of claim 1, wherein the alumina contains an acidic modifier.

16. The method of claim 1, wherein the alumina has an average crush strength of 0.5 to 40 kg.

* * * * *